(12) United States Patent
Guadalupe et al.

(10) Patent No.: US 6,231,920 B1
(45) Date of Patent: May 15, 2001

(54) ELECTROANALYTICAL APPLICATIONS OF SCREEN-PRINTABLE SURFACTANT-INDUCED SOL-GEL GRAPHITE COMPOSITES

(75) Inventors: Ana R. Guadalupe; Yizhu Guo, both of San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 09/181,875

(22) Filed: Oct. 29, 1998

Related U.S. Application Data
(60) Provisional application No. 60/063,160, filed on Oct. 29, 1997.

(51) Int. Cl.[7] .................................................. B05D 1/32
(52) U.S. Cl. .............................. 427/122; 427/282; 427/287
(58) Field of Search ...................... 427/2.11, 58, 122, 427/282, 287; 204/403, 294; 600/372; 252/510, 511

(56) References Cited

U.S. PATENT DOCUMENTS

| | | |
|---|---|---|
| 4,229,490 | 10/1980 | Frank et al. |
| 5,160,418 * | 11/1992 | Mullen . |
| 5,403,462 | 4/1995 | Lev et al. |
| 5,494,562 * | 2/1996 | Maley et al. |
| 5,529,676 | 6/1996 | Maley et al. |
| 5,573,647 | 11/1996 | Maley et al. |
| 5,582,698 | 12/1996 | Flaherty et al. |
| 5,601,694 | 2/1997 | Maley et al. |
| 5,616,222 | 4/1997 | Maley et al. |
| 5,711,868 | 1/1998 | Maley et al. |
| 5,770,028 | 6/1998 | Maley et al. |

OTHER PUBLICATIONS

Kalcher, K.; Kaufmann, J. M.; Wang, J.; Vytras, K.; Neuhold, C.; Yang, Z. *Electroanalysis* 1995, 7, No. 1, pp. 5–22.
Bilitewski, U.; Ruger, P.; Schmid, R. D., *Biosens. & Bioelectron.* 1991, 6, pp. 369–373.
Ikegami, A.; Arima, H.; Iwanaga, S.; Kaneyasu, M., *Proceedings of the 4th European Hybrid Microelectronic Conference,* Copenhagen, May 18–20, 1983, pp. 211–218.
Alvarez–Icaza, M.; Bilitewski, U., *Anal. Chem.* Jun. 1993, vol. 65, No. 11, pp. 525A–533A.
Kalcher, K., *Electroanalysis* 1990, 2, pp. 419–433.
Tsionsky, M.; Lev. O., *Anal. Chem.* 1995, 67, pp. 2409–2414.
Tsionsky, M.; Gun. G.; Glezer, V.; Lev, O. *Anal. Chem.* 1994, 66, pp. 1747–1753.
Sampath, S.; Lev. O. *Anal. Chem.* 1996, 68, pp. 2015–2021.
Iosefzon–Kuyavskaya, B; Gigozin, I.; Ottolenghi, M.; Avnir, D.; Lev. O., *J.Non–Cryst, Solids* 1992, 147 & 148, pp. 808–812 (North Holland).

(List continued on next page.)

Primary Examiner—Fred J. Parker
(74) *Attorney, Agent, or Firm*—Patent Law Office of Heath W. Hoglund

(57) ABSTRACT

A process for preparing sol-gel graphite composite electrodes is presented. This process preferably uses the surfactant bis(2-ethylhexyl) sulfosuccinate (AOT) and eliminates the need for a cosolvent, an acidic catalyst, a cellulose binder and a thermal curing step from prior art processes. Fabrication of screen-printed electrodes by this process provides a simple approach for electroanalytical applications in aqueous and nonaqueous solvents. Examples of applications for such composite electrodes produced from this process include biochemical sensors such as disposable, single-use glucose sensors and ligand modified composite sensors for metal ion sensitive sensors.

8 Claims, 10 Drawing Sheets

OTHER PUBLICATIONS

Dunuwila, D.C.; Torgerson, B.A.; Chang, C.K.; Berglund, K.A.., *Anal. Chem.* 1994, 66, pp. 2739–2744.

Dunbar, R.A.; Jordan, J.D.; Bright, F.V. *Anal. Chem.* 1996, 68, pp. 604–610.

Petit–Dominguez, M.D.; Shen, H.; Heineman, W.R.; Seliska, C.J., *Anal. Chem.* 1997, 69, pp. 703–710.

Wang, J.; Pamidi, P.V.A.; Park, D.S., *Anal. Chem.* 1996, 68, pp. 2705–2708.

Avnir, D., *Acc. Chem. Res.* 1995, 28, pp. 328–334.

Avnir, D.; Braun S.; Lev. O.; Ottolenghi, M., *Chem. Mater* 1994, 6, pp. 1605–1614.

Zink, J. I.; Yamanaka, S. A.; Ellerby, L. M.; Valontine, J. S.; Nishida, F.; Dunn, B. J., *Sol–Gel Sci. Technol.* 1994, 2, pp. 791–795.

Hench, L. L.; West, J. K., *Chem. Rev.* 1990, 90, pp. 33–72.

Brinker, C. J.; Hurd, A. J.; Schunk, P. R.; Frye, G. C.; Ashley, C. S., *J. Non–Cryst, Solids* 1992, 147 & 148, pp. 424–436.

Cardosi, M.F.; Birch, S.W., *Anal. Chim. Acta* 1993, 276, pp. 69–74.

Avnir, D.; Kaufman, V. R.; Feisfeld, R., *J. Non–Cryst. Solids* 1985, 74, pp. 395–406.

Green, MI; Hilditch, P.I., *Anal.Proc.* 1991, 28, pp.374–376.

Turner, A.D.F., *Anal Proc.,* 1991, 28, pp. 376–377.

Adams, R.N., *Anal Chem.* Sep. 1958, 30, p. 1576.

Gorton, L., *Electroanalysis* 1995, 7, No. 1, pp. 23–45.

Creasy, K.E.; Shaw.B.R., *Anal. Chem.* 1989, 61, pp. 1460–1465.

Wang, J.; Golden, T.; Varughese, K. El–Reyes, I., *Anal. Chem.* 1981, 61, pp. 508–512.

Wang, J.; Varughese, K.., *Anal. Chem.* 1990, 62, pp. 318–320.

Shaw, B.R.; Creasy, K.E., *Anal. Chem.* 1988, 60, pp. 1241–1244.

Alegret, S.; Cespedes, F.; Martinez–Fabregas, E.; Martorell, D.; Morales, A.; Centelles, E.; Munoz, J.,*Boisens. & Bio-electron.,* 1996, 11, pp. 35–44.

Alegret, S., *Analyst* 1996, 121, pp. 1751–1758.

Wring, S.A.; Hart, J.P.; Birch, B.J., *Analyst* 1989, 114, pp. 1563–1570.

Wring, S.A.; Hart, J.P.; Birch, B.J., *Electroanalysis* 1992, 4, p.299–309.

Wring, S.A.; Hart, J.P.; Birch, B.J. *Analyst,* Feb. 1991, 116, pp. 123–129.

Baldwin, R.; Christensen, J.; Kryger, L., *Anal. Chem.* 1986, 58, pp.1790–1798.

Brinker, C.J.; Scherer, G.W., *Sol Gel Science,* Academic Press, San Diego, 1990, pp.vii–x.

Kasem, K.K.; Abruna, H.D. *J. Electroanal. Chem.* 1988, 242, pp. 87–96.

Gao, Z.; Wang, G.; Li, P.; Zhao, Z., *Anal Chem.* 1991, 63, pp. 953–957.

Guadalupe, A.R.; Abruna, H.D., *Anal. Chem.* 1985,57, pp. 142–149.

Wier, L.M.; Guadalupe, A.R.; Abruna, H.D., *Anal. Chem.* 1985, 57, 2009–2011.

Neuhold, C.; Wang, J.; Cai, X.; Kalcher, K.., *Analyst* 1995, 120, pp. 2377–2380.

Nehould, C.; Wang, J.; Nascimento, V.; Kalcher, K., *Talanta,* 1995, 42, pp. 1791–1798.

Wang, J.; Nascimeno, V.B.; Lu, J.; Park, D.S. Angnes, L., *Electroanalysis* 1996, 8, No. 7, pp. 635–638.

Prabhu, S.V.; Baldwin, R.P., *Anal. Chem.* 1987, 59, pp. 1074–1078.

Rohm, I.; Kunnecke, W.; Bilitewski, U. *Anal. Chem.* 1995, 67, pp. 2304–2307.

Guo, Yizhu, Guadalupe, Ana R., *Sensors and Actuators* B 46 (1998) pp. 213–219.

P. V.A. Pamidi, "Structurally and Chemically Modified Sol–Gel Carbon Thick Film Glucose Sensors", *Polymeric Materials Science and Engineering,* Spring Meeting, Apr. 1997, vol. 76, Apr. 1997, pp. 513–514.

J. Gun, "Sol–Gel Derived Ferrocenyl–Modified Silicate–Graphite Composite Electrode: Wiring of Glucose Oxidase", *Analytica Chimica ACTA,* vol. 336, No. 1–3, 1996, pp. 95–106.

\* cited by examiner

ELECTROANALYTICAL APPLICATIONS OF SCREEN-PRINTABLE SURFACTANT-INDUCED SOL-GEL GRAPHITE COMPOSITES

This application claims the benefit under 35 USC 119(c) of provisional patent application No. 60/063,160, filed Oct. 29, 1997.

The subject matter of this invention was made with the financial support of the U.S. government, under the following grants: DOE-EPSCOR (Grant number 046138) and NIH-MBRS Program (Grant Number S06 GM 08102). The U.S. government has certain rights in this invention.

This invention relates to a novel process for preparing sol-gel graphite composite electrodes, and to the composite electrodes produced therefrom.

Carbon paste and graphite composites with their unique properties of easy and bulk modification, renewable surface and low background currents have found wide applications in electrocatalysis and electroanalysis. Carbon inks are commonly and commercially used for the microfabrication of electrochemical sensors and biosensors based on thick-film technologies. The selectivity of these surfaces is enhanced by their modification with a recognition entity chosen according to the analytes to be determined. The simple mixing of the surface modifier with the graphite before the electrode assembly has always presented the problem of modifiers leaching with concomitant detrimental effects on the electrochemical response. Recently, sol-gel graphite composite electrodes have been reported for biosensors and chemical sensors and procedures for screen-printed electrodes with these composites. Sol-gel networks are promising encapsulation matrices because mild polymerization conditions and low gelation temperatures can be used allowing the encapsulation of fragile biological molecules. Furthermore, properties such as porosity, hydrophilicity and matrix chemical modification can be controlled in the preparation process to avoid the leaching problem and enhance the analyte diffusion and selectivity.

Generally, sol-gel reactions proceed by hydrolysis of an alkoxide precursor under acidic or basic conditions, and subsequent condensation of the hydroxylated monomers to form a porous gel. The addition of a co-solvent is necessary to mix the alkoxide with water.

SUMMARY OF THE INVENTION

To avoid the previously discussed problems, the present invention is directed to a novel process for preparing sol-gel graphite composite electrodes, which comprises introducing a surfactant into the process and thus avoiding the need for a co-solvent, a catalyst, a cellulose binder and thermal curing. This process is more environmentally friendly and compatible for organics and biomolecules immobilization, and offers an economical one-step fabrication of screen-printed modified electrodes. Additionally, composite electrodes produced from this novel process exhibit improved properties previously not taught in the prior art. Specifically, the resulting composite electrodes have a fine texture, and exhibit excellent adhesion and mechanical strength when exposed to both aqueous and non-aqueous solutions.

Because composites generally have low electrical resistance and good adhesion to various substrates (e.g., PVC, ceramics, metals, glass), this procedure offers an economical, one-step and low cost fabrication of screen-printed modified electrodes. Therefore, a further object of the present invention is to demonstrate electroanalytical applications of this composite in electrocatalysis and electroanalysis, specifically for composite electrodes in chemical sensors and biosensors.

Biosensors have been in the market place for several years, of which glucose sensors have prevailed, creating a large and stand-alone business. Disposable single-use sensors are one of the main products used by diabetic patients. However, to be more competitive with the existing methodologies on a large scale, many aspects should be improved to make them less expensive, user and environment friendly, and more easily manufactured (less complex to readily control quality and cut costs). Printing inks are obviously one of the critical components determining the products' performance and acceptance. And many efforts have been made in this field. UV-polymerizable screen-printable composites have been produced for more durable enzyme sensors. Screen-printable sol-gel enzyme-containing carbon inks offer a one-step fabrication of disposable enzyme strips obviating the need for thermal curing.

Besides the low cost and easy fabrication, the mediated glucose sensor that can be prepared in accordance with the present invention possesses excellent characteristics such as low operation potential (+0.3 V) and therefore less interferences, a wide working range (up to 30 mM) with a linear range up to 15 mM, a short response time (around 10 seconds) and long-term stability and shelf time.

In accordance with the present invention, disposable complexing (pre-concentrating) screen-printed strip electrodes for trace nickel have been fabricated by doping a sol-gel graphite composite with ligand dimethylglyoxime. Optimum quantitation procedures and parameters have been identified. A short (1 minute) accumulation period using open-circuit condition yielded a detection limit of 2 $\mu$g/L nickel. Fabrication of screen-printed environmental sensors by incorporation of ligands into carbon inks holds promise in routine trace metal speciation and quantitation based on the conventional pre-concentration/voltammetric strategy. For example, cobalt phthalocyanine (CoPC) modified composite electrode shows a behavior different from previous studies, indicating differences in charge and mass transport of species in these composite electrodes compared to traditional carbon paste electrodes. In addition, the surfactant-induced sol-gel polymerization that occurs in accordance with the present invention allows the encapsulation of fragile molecules under relatively mild conditions. This polymerization beneficially results in a mechanically and chemically stable surface for organic solvents.

Additional features and advantages of the present invention will be set forth in part in the description that follows, and in part will be apparent from the description, or may be learned by practice of the invention. The objectives and other advantages of the present invention will be realized and attained by means of the elements and combinations particularly pointed out in the written description and appended claims.

BRIEF DESCRIPTION OF THE DRAWINGS

FIG. 1 illustrates a cyclic voltammogram of ferrocene in acetonitrile at the unmodified SSCEs when the solution comprises 5 mM Fc, 0.1M TEATS, wherein the scan rate is 20 mV/s.

FIG. 2 illustrates a cyclic voltammogram of reduced glutathione at the unmodified SSCEs when the solution comprises (a) pH5.5 PBS; (b) a+6.76 mM GSH; (c) a+15.67 mM GSH, wherein the scan rate is 10 mV/s.

FIG. 3 illustrates a cyclic voltammogram of reduced glutathione at the CoPC modified SSCEs when the solution comprises pH 5.5 PBS containing (a) 0.0, (b) 1.98, (c) 4.88, (d) 8.16, (e) 12.21, (f) 15.67 mM GSH, and the scan rate is 10 mV/s.

FIG. 4 illustrates the corresponding calibration plot from FIG. 3.

FIG. 5 illustrates the dependence of the OSW peak current on the accumulation time in a quiescent $Ni^{2+}$ solution (2.0 µM) at open circuit.

FIG. 6.

FIG. 7 illustrates a cyclic voltammogams of (Ferrocence+GOx) modified (solid curves) and unmodified (dashed and dotted curves) SSCEs in PBS (pH 6.95) containing 0.0 mM glucose (curve a and dashed curve) and 10.0 mM glucose (curve b and dotted curve), with a scan rate of 5 mV/s.

FIG. 8 illustrates chronoamperometric responses of (ferrocence+GOx) modified (b) and unmodified (a) SSCEs to successive addition of 0.8 mM glucose when the solution comprises PBS (pH 6.95), uses a stirring rate of 250 rpm, and an applied potential of +0.3 V.

FIG. 9 illustrates calibration plots for the (ferrocence+GOx) modified SSCEs at different applied potentials.

DETAILED DESCRIPTION OF THE INVENTION

Figure 1:
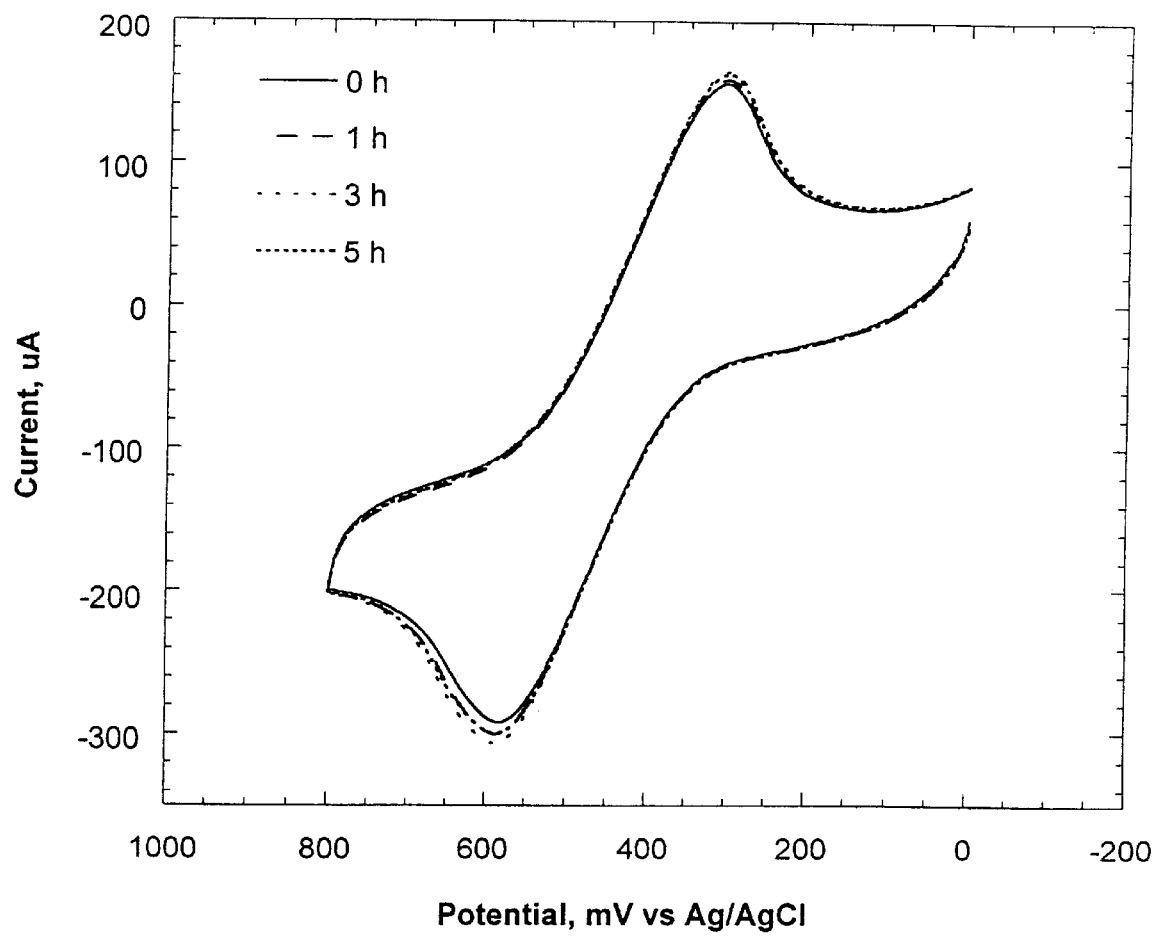
FIG. 1.

This invention as broadly described above is directed to a method of producing surfactant-induced, sol-gel graphite composite electrodes by mixing an aqueous solution of a silane or a siloxane with a surfactant to get a clear and homogeneous sol solution. Specifically, Applicants have discovered that by incorporating a surfactant into the sol solution, the need for a co-solvent, a catalyst, or a cellulose binder is eliminated. Elimination of these components in turn eliminates the need for a thermal curing process that has been required until now when producing such electrodes.

Once a homogeneous sol solution is achieved, it is mixed with a graphite powder to form a uniform and free-flowing paste and applied to a substrate to form at least one electrode. Preferably, several electrodes can be formed at one time. While screen printing has been used to produce advantageous electrodes, this step may be performed using other traditional thick-film techniques.

This invention is further directed to a surfactant-induced, sol-gel graphite composite electrode. Applicants have discovered that such surfactant-induced electrodes can be fabricated into smooth films that exhibit high adhesion, mechanical strength and stability on the substrate to which they are applied. Such electrodes have the unexpected property of being stable in both aqueous and non-aqueous solutions.

Surfactant-induced sol-gel graphite-composites were prepared and analyzed using a variety of materials in accordance with the invention. Various silanes and siloxanes, including tetramethyl orthosilicate (TMOS), methyltrimethoxysilane, tetraethoxysilane, and methyltriethoxysilane, and different surfactants, including bis(2-ethylhexyl) sulfosuccinate, i.e., Aerosol OT (AOT), an octylphenol ethylene oxide condensate, i.e., Triton X-100, cetyltrimethylammonium bromide (CTAB), and sodium dodecylsulfate (SDS) were tested as components of the sol solution. Advantageous and unexpected results were obtained for the (AOT+TMOS) systems, with respect to the viscosity, gelation time, mechanical strength, and compatibility with the graphite powder.

AOT in the system may act as a catalyst for the sol-gel formation, and a dispersing agent for homogenizing the carbon particles and incorporated reagents. Addition of surface active agents during sol-gel process are known to result in greatly improved homogeneity, remarkably smooth surface texture, and high adhesion between gel film and substrates. The introduction of AOT eliminates the use of such additives as alcohol cosolvents, acid catalyst, and cellulose binders, which simplifies the fabrication processes. For example, the elimination of such additives reduces the parameters influencing the final products' performances. In turn, the complexity and cost are reduced.

The following materials are advantageously used in accordance with the present invention: Ferrocene from Alfa Chemicals; Acetonitrile (water content less than 0.001%) from Burdick and Jackson; Glucose, glucose oxidase (GOx, EC 1. 1.3.4, from *Aspergillus niger,* 166,100 units/g), and glutathione (reduced form, GSH) from Sigma; Cobalt phthalocyanine (CoPC), bis(2-ethylhexyl) sulfosuccinate (sodium salt, AOT) from Fluka; Graphite powder (Grade #38) from Fisher Scientific; Tetramethyl orthosilicate (TMOS) from Aldrich; Dimethylglyoxime (DMG) from Matheson Coleman and Bell; Nickel ammonium sulfate from J. T. Baker; Tetraethylammonium 4-toluenesulfonate (TEATS) from Acros. The reagents should be at least analytical reagents and can be used as received. All aqueous solutions were prepared using nanopure water (18 Ω.cm). PVC (48"×96"×1 mm, Sintra sheet-white) from United States Plastic Corp. Ceramic sheets (4.5 inch×4.5 inch×0.45 mm) obtained from Coors Ceramics Company.

Apparatus Used for Electrode Measurements

Voltammetric (cyclic and Osteryoung square wave (OSWV)) and amperometric measurements were carried out at room temperature with a Bioanalytical Systems Model 100 B/W potentiostat in a 10-ml cell containing a SSCEs working electrodes, a Ag/AgCl (3M NaCl) reference electrode and a Pt wire auxiliary electrode. All potentials in the text are referred to the Ag/AgCl electrode without regard for the liquid junction. pH measurements were made with a φ50 pH meter (Beckman).

Preparation of Sol-gel Graphite Mixtures

Sol-gel graphite mixtures were prepared using the following procedures. The mixing of $AOT:TMOS:H_2O$ (1:50:200, molar ratio) readily gave a clear and homogeneous solution. Immediately prior to use, 1 ml of the sol solution prepared above was added to 0.6 g graphite powder in a small glass vial and well mixed for about 3 minutes to give a uniform free-flowing paste.

For the modified electrodes, a modifier or recognition entity that included ferrocene was used. The ferrocene was first dissolved in ethanol. After the solvent evaporated, an enzyme was added. More specifically, prior to addition of the sol, the graphite powder was mixed with ferrocene (2.5%, w/w expressed as ferrocene with respect to graphite) which was first dissolved in ethanol, glucose oxidase (5%) buffer solution or cobalt phthalocyanine (5%), dimethylglyoxime (10%) ethanol solution, and then dried at room temperature.

Preparation of Electrodes by Screen Printing

After the sol-gel step, a preferred method of screen-printing the modified and non-modified graphite electrodes proceeded in the following manner. A home-mace screen-printer was used to fabricate the surfactant-induced sol-gel derived carbon working electrodes (SSCEs). Pretreated PVC or ceramic sheets were used as substrates. Pretreatment preferably included coating the substrate with a clear nail polish. The paste was printed onto the pretreated PVC substrates (2.5×4.0 cm) to yield eight strips of 2.5×0.5 cm with 2.0×0.15 cm working electrode pattern. A portion of the electrode surface was covered with nail-polish insulating layer, leaving 0.1 $cm^2$ area on both ends for defining the working electrode and the electrical contact. For applications in organic solvents, the insulating layer was wrapped with Parafilm (American National Can).

Preparation of Buffered Solutions

Buffered solutions were subsequently prepared for further studies. Phosphate buffer (PBS) was used for glucose determinations (pH 6.95) and glutathione (GSH) determinations (pH 5.5). A 0.1M ammonia buffer solution (pH 9.2) served as the supporting electrolyte for nickel quantitation. Acetonitrile containing 0.1M TEATS was employed for the non-aqueous electrochemical studies.

Evaluation of Electrodes

Electrodes fabricated from the surfactant-induced sol-gel composites prepared in accordance with the present invention were evaluated and found to be mechanically strong. They also possessed a high adhesion to ceramics, glass and metal sheets, and weighing paper except PVC, on which the coated film was readily cracked and peeled off. However, due to its low cost and better processing characteristics, PVC is one of the most commonly and commercially used substrates in the fabrication of screen-printed strips. It was found that excellent performance (high adhesion, mechanical strength and stability, and smooth film) was obtained with slightly pretreated PVC substrates. Therefore, the pretreated PVC was used as substrate in the examples presented herein.

Evaluation of Electrical and Microstructural Properties

The screen-printed carbon strips were evaluated and found to have low electrical resistance. They gave resistance values of approximately 100 Ω over a 1-cm electrode length, obviating the need for a conducting metal layer and thermal curing. They thus provide a rapid and economical one-step fabrication of screen-printed electrodes. Scanning electron micrograph studies revealed a microporous structure of the electrode surface with particles of different size, reflecting a high surface area.

Evaluation of Stability in Organic Solvent

The stability of the inventive sol-gel graphite composite electrodes in organic solvent was evaluated. Carbon paste electrodes or robust carbon composite electrodes are usually made of carbon powder dispersed in organic polymers, e.g., wax, epoxy, poly(chlorotrifluoroethylene)) or organic liquids, e.g., paraffin oil, silicone, Nujol, grease. The use of organic binders has generally hindered their applications in nonaqueous solutions due to their dissolution. Sol-gel graphite composite electrodes in accordance with the present invention are a reasonable alternative to this problem, because the inorganic matrices thereof are stable in both aqueous and nonaqueous media. To investigate the stability of the surfactant-induced sol-gel graphite composite electrodes of the present invention in organic solvents, the electrochemistry of ferrocene (Fc) in acetonitrile (AN) was studied with the SSCEs. FIG. 1 shows the cyclic voltammograms of Fc in AN at unmodified SSCEs after 1, 3 and 5 hours of immersion in stirred AN solution. There was a slight increase in the peak current after 1 hour immersion. This may have been due in part to some dissolution of the surfactant, which increased the electrode area. Another possibility is the dissolution of the insulating nail-polishing layer, which would also expose a greater electrode surface area. There were no obvious differences between the second, the third and the fourth cycles; thereby demonstrating a high stability of the composite electrodes in organic solvents.

The invention is illustrated in greater detail in the following, non-limiting examples.

EXAMPLE 1. Electrodes for Electrocatalytic Applications

Figure 2:
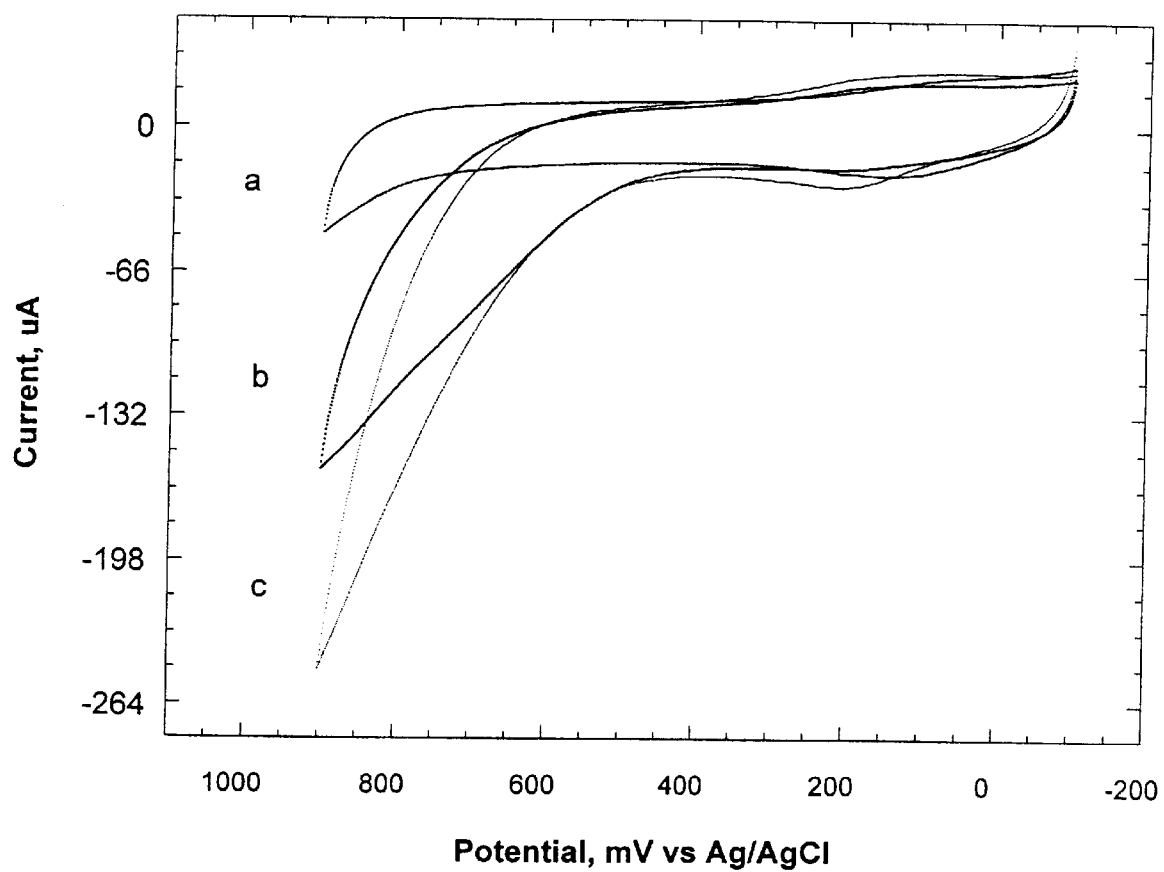
FIG. 2.
Figure 3:
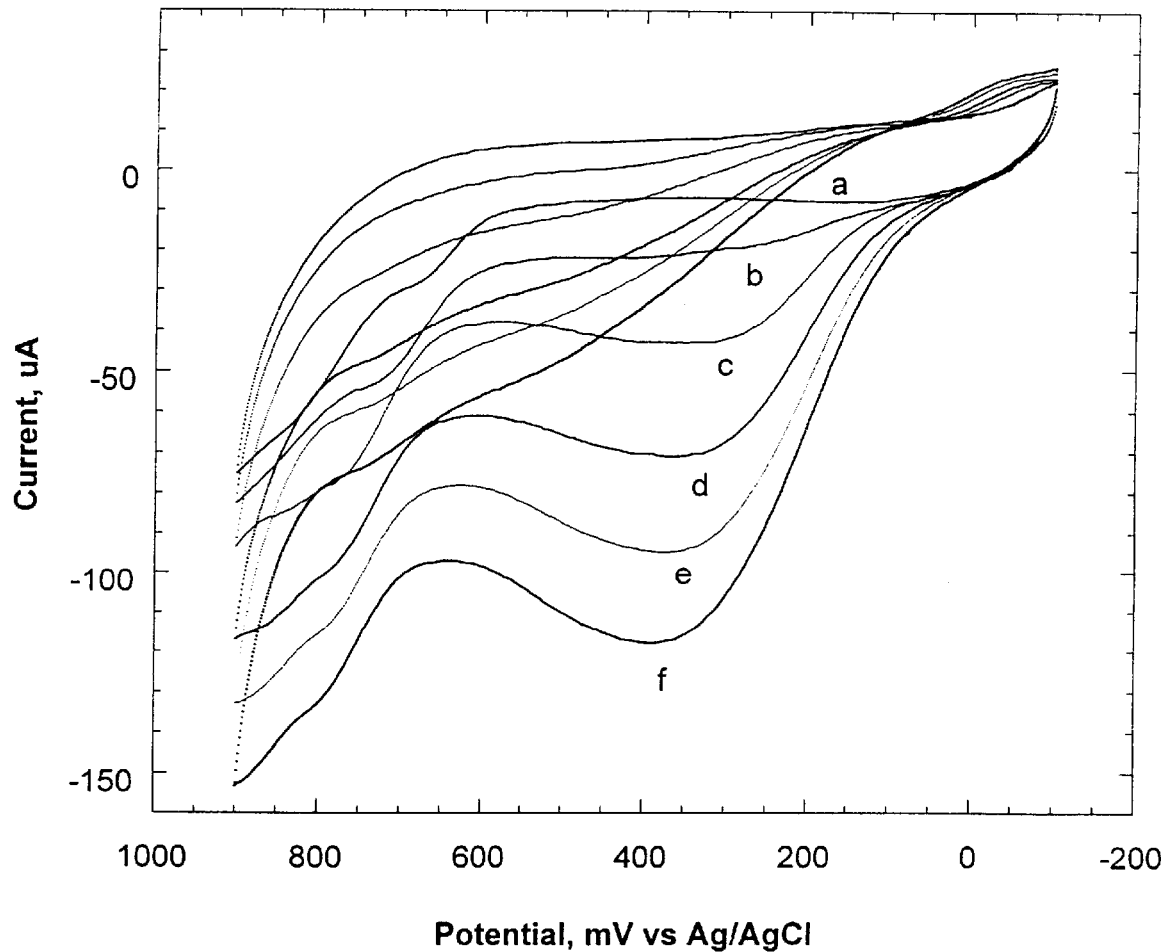
FIG. 3.
Figure 4:
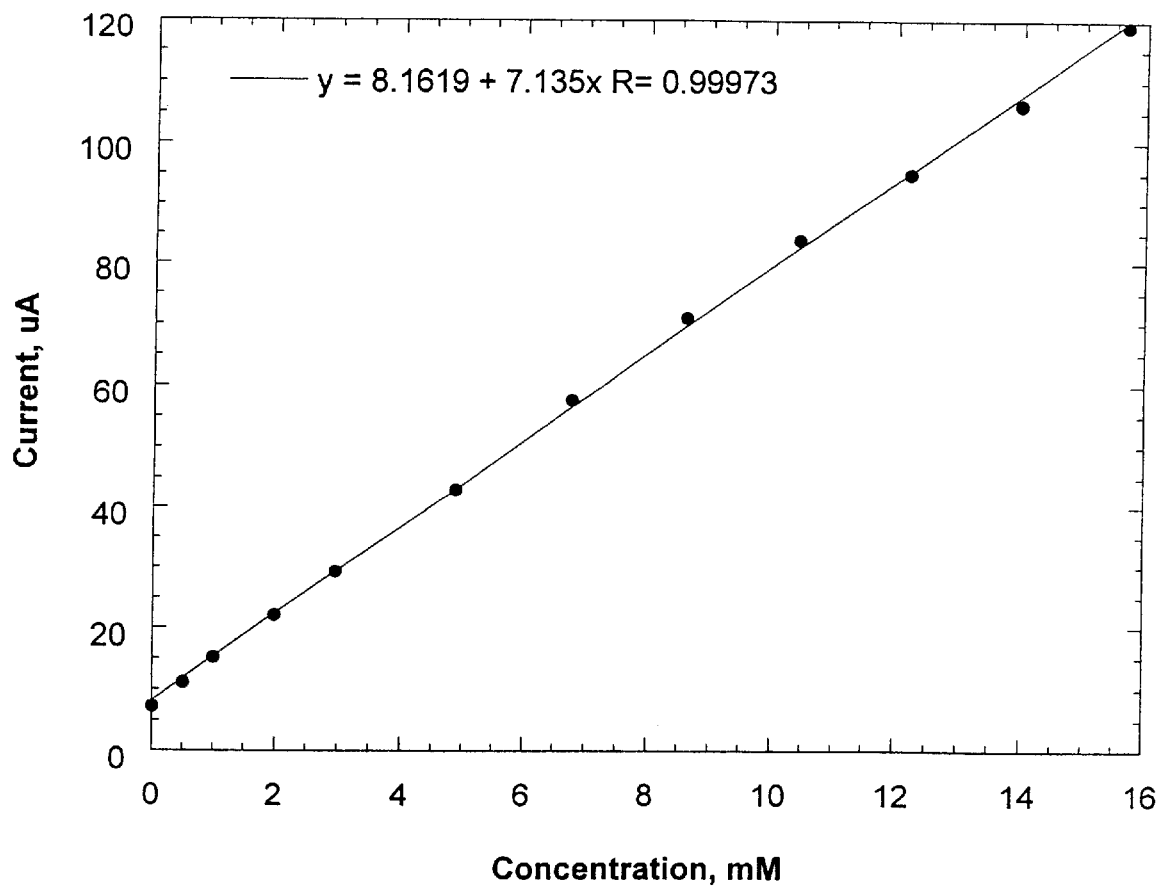
FIG. 4.

To demonstrate the potential use of the electrode surfaces of the electrodes prepared in accordance with the present invention for catalyst immobilization, cobalt phthalocyanine (CoPC) was immobilized into the SSCEs and used in the electrocatalytic determination of GSH. FIG. 2 shows the cyclic voltammograms of GSH at the unmodified SSCEs. The onset potential for the direct oxidation of GSH at this electrode was about +0.4 V, as demonstrated by an anodic current increase as a function of GSH concentration when the applied potential exceeded +0.6 V. Meanwhile, at the CoPC modified electrodes, the electrocatalytic current started rising at potentials +0.05 V, and an anodic peak was observed around +0.35 V (see FIG. 3). The peak current was found to be proportional to the GSH concentration up to 15 mM, as shown in FIG. 4. The immobilized CoPC acted as a mediator, accelerating the rate of GSH oxidation at low overpotentials. On these experiments, two anodic weaves were observed, e.g., ca.+0.3 V and +0.78 V at a CoPC modified electrode. The peak at +0.3 V, occurring only in the presence of GSH, was assigned to the oxidation of $Co^1$ to $Co^{11}$ and the peak at +0.78 V, occurring in the absence and presence of GSH, was considered to be the oxidation of $Co^{11}$ to $Co^{111}$. The current at +0.78 V was about 3 times higher than that at +0.3 V previously discussed in the art while the anodic wave at +0.3 V was better developed on SSCEs. The higher efficiency of the $Co^1/Co^{11}$ center may have been due to more accessibility of the catalyst incorporated in the porous SSCEs and higher conductivity of the SSCEs matrix, which appeared to facilitate the mass transport and electron transfer.

EXAMPLE 2. Metal Ion Sensitive Electrodes

While most electroanalytical applications of chemically modified electrodes have been focused on electrocatalysis, a few have employed pre-concentration/voltammetric strategy based on immobilized ion exchangers, organic coordinating ligands, clays, etc., which have shown great analytical promise, especially for the speciation and quantitation of trace metals in environmental monitoring and control. For example, complexation and quantitation of lead was performed with DPT modified SSCEs. In addition, to demonstrate the feasibility to construct disposable metal ions sensitive electrodes with SSCEs, dimethylglyoxime (DMG) was incorporated into the SSCEs for the detection of trace nickel.

The quantitation procedure comprised three steps: the accumulation, measurement, and cleaning steps. For the $Ni^{2+}$ pre-concentration, the electrode was immersed in the stirred or quiescent sample solution for a few minutes at an open circuit or at an applied potential. Then, the accumulated nickel was measured by Osteryoung Square Wave Voltammetry (OSWV) in pH 9.2 ammonia buffer. Last, following each measurement, the electrode was immersed in 0.1M HCl solution for a 30 seconds cleaning step and then rinsed with water.

The accumulation conditions advantageously influence, and/or optimize, sensor response time, sensitivity and the detection limit. Accumulation in stirred or quiescent solution at open circuit or a certain applied potential was investigated.

Table 1 shows the electrode response under different accumulation conditions.

TABLE 1

Electrode Responses Under Different Accumulation Conditions with the DMG Modified SSCEs

| conditions* | 1 | 2 | 3 | 4 |
|---|---|---|---|---|
| unstirred | √ | | | √ |
| stirred | | √ | √ | |
| open circuit | √ | √ | | |
| applied potential (−0.5 V) | | | √ | √ |
| current (μA) | 0.96 | 1.39 | 1.18 | 0.92 |

*Accumulation time: 1 min; Accumulation solution: [$Ni^{2+}$] = 5 × $10^{-7}$ M.

Figure 5:
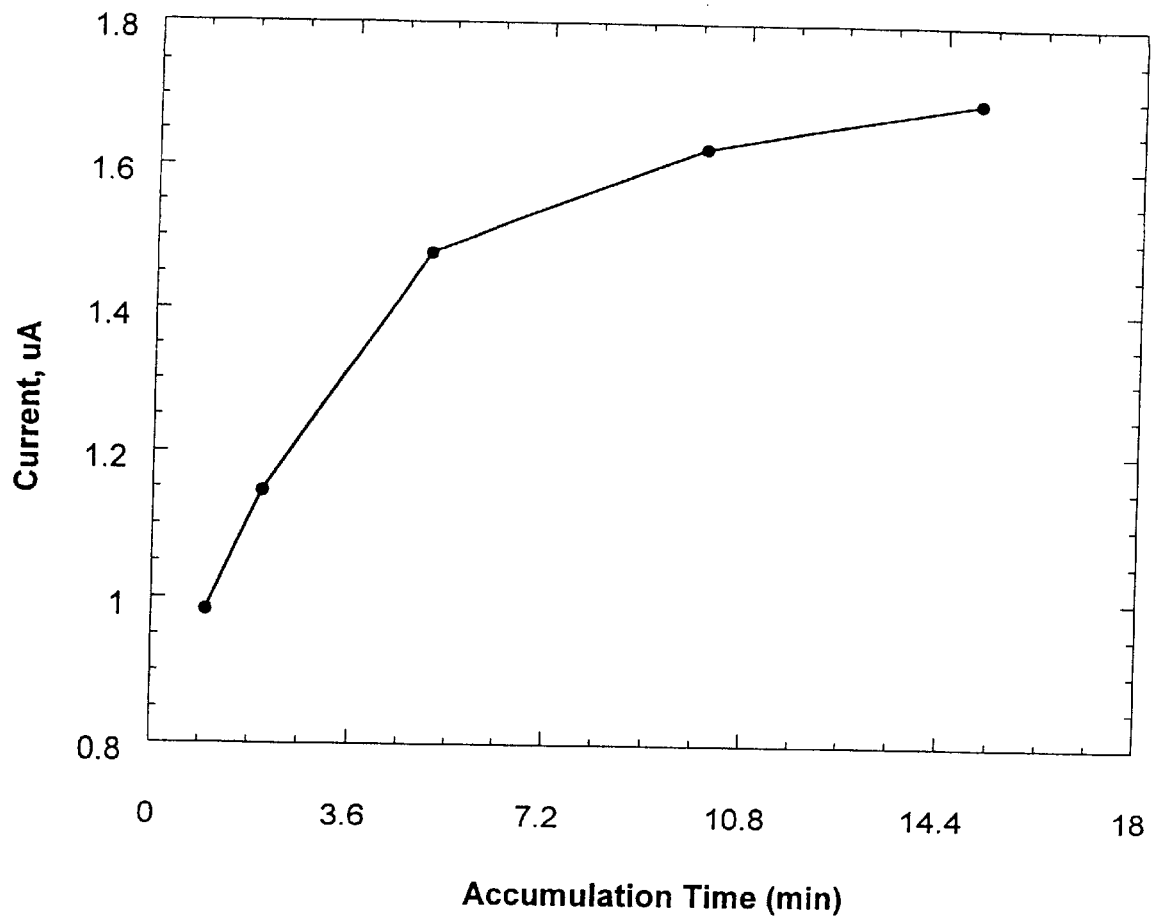
FIG. 5.

As can be seen from the results presented in Table 1, accumulation in a stirred solution at an open circuit gave the highest sensitivity, which was comparable to the response observed in the unstirred solution or under an applied −0.5 volts. These results suggest that the use of an applied potential may be unnecessary. FIG. 5 shows the dependence of response current on accumulation time in quiescent solutions at an open circuit. FIG. 5 shows that 5 minutes accumulation in quiescent solution gave comparable results with the 1 minute in stirred solution.

Figure 6A:
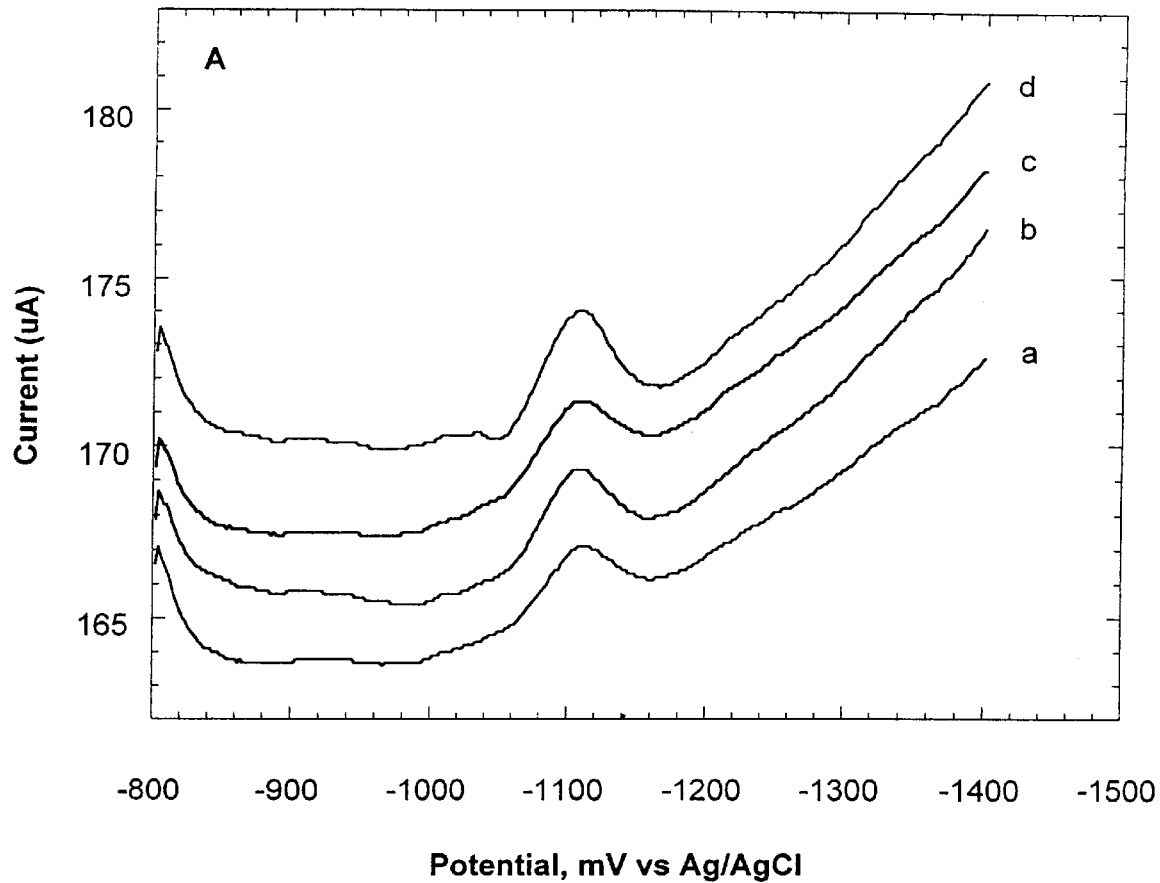
FIG. 6A illustrates Osteryoung square wave voltammetric responses of the DMG modified SSCEs for various nickel concentrations when the solution is ammonia buffer (pH 9.2) containing (a) 0.1, (b) 0.2, (c) 0.3, and (d) 0.4 µM $Ni^{2+}$, the scan ratio is 10 mV/s, the amplitude is 25 mV, the accumulation condition is a 1 min in-stirred solution.
Figure 6B:
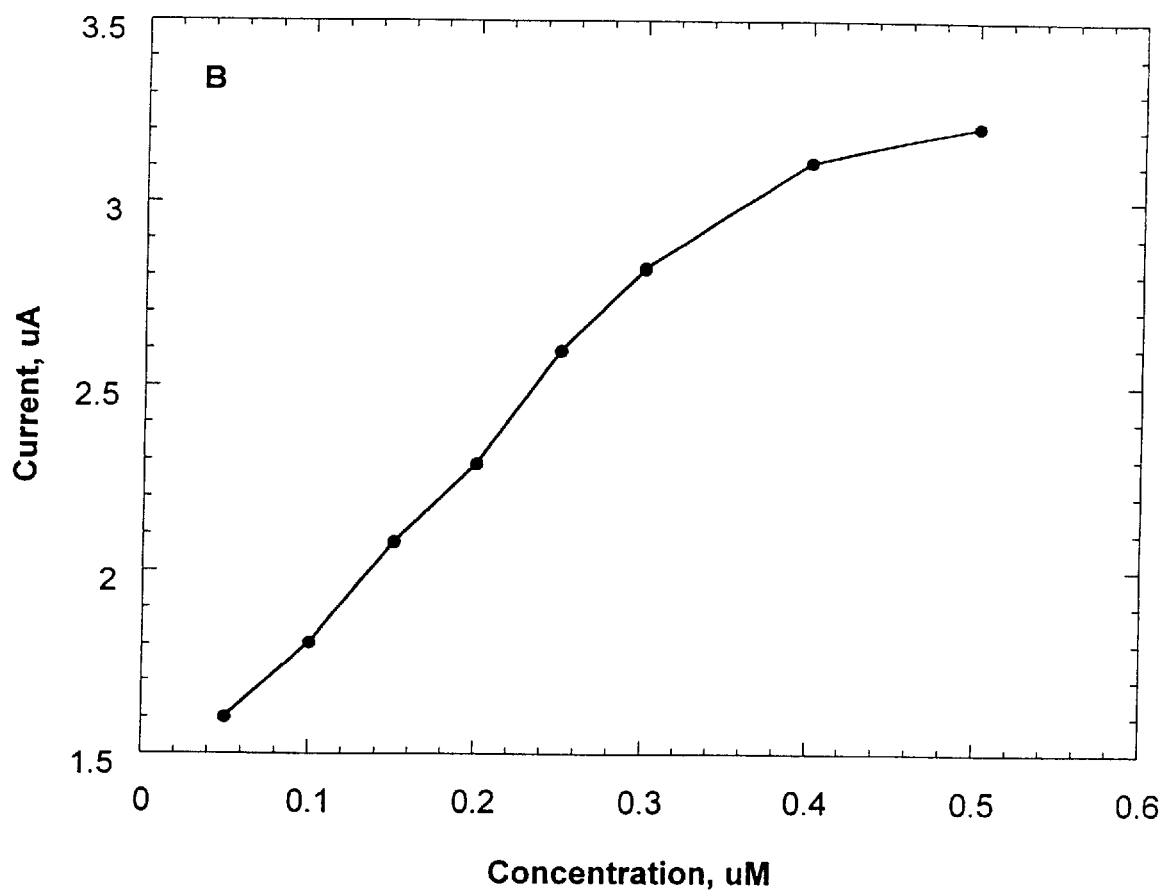
FIG. 6B represents a corresponding calibration plot.

One minute accumulation in stirred solution was used in the following evaluation. FIG. 6 shows the Osteryoung square wave voltammetric responses of the DMG-modified SSCEs for various nickel concentrations and the corresponding calibration plot. Well-defined peaks were obtained over this low concentration range. Linear responses were attained between 0.05 and 0.3 μM. A detection limit of 0.02 μM (about 2 μg/L) was achieved under these quantitation conditions.

EXAMPLE 3. Mediated Glucose Biosensor

Figure 7:
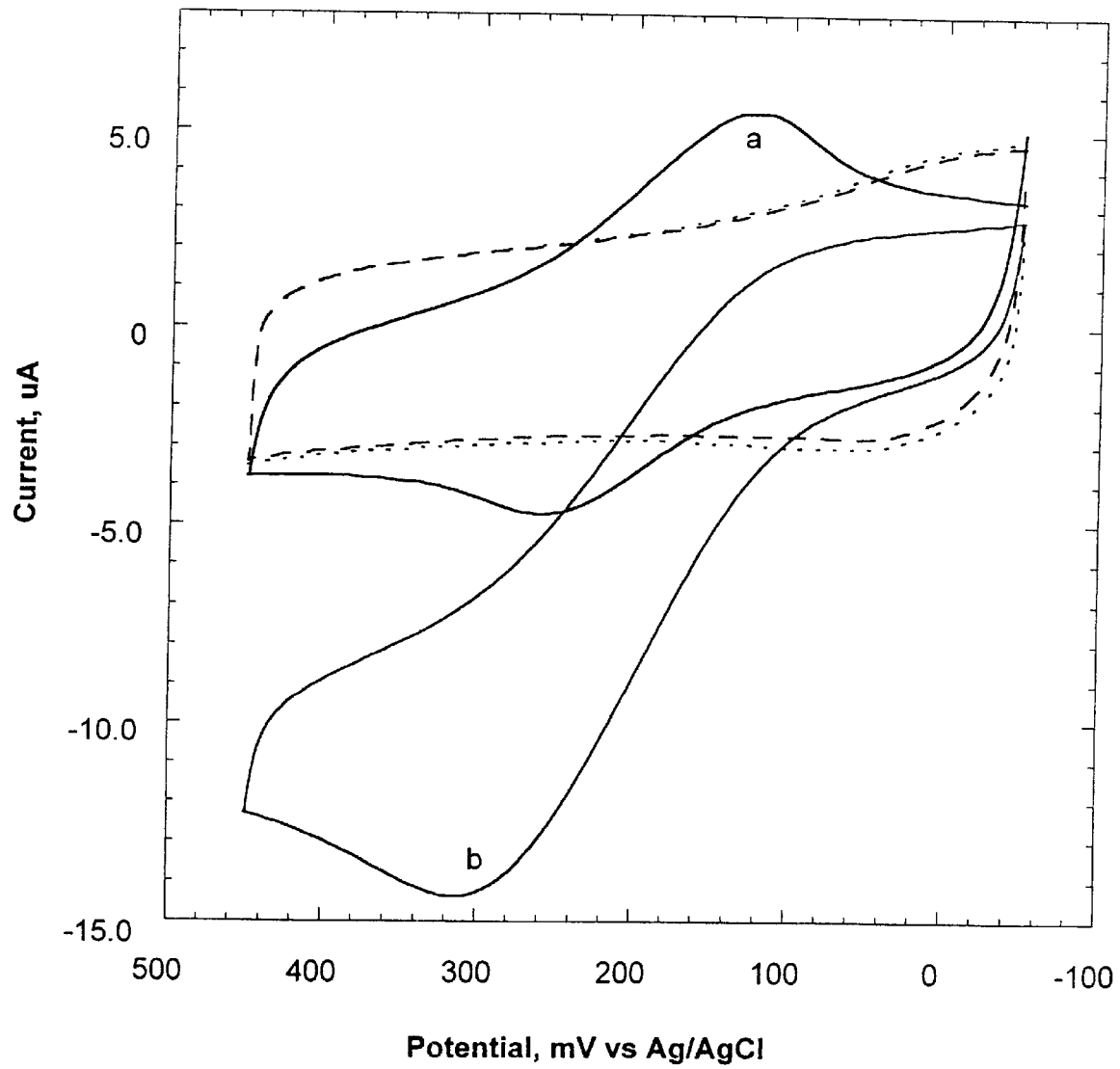
FIG. 7.
Figure 8:
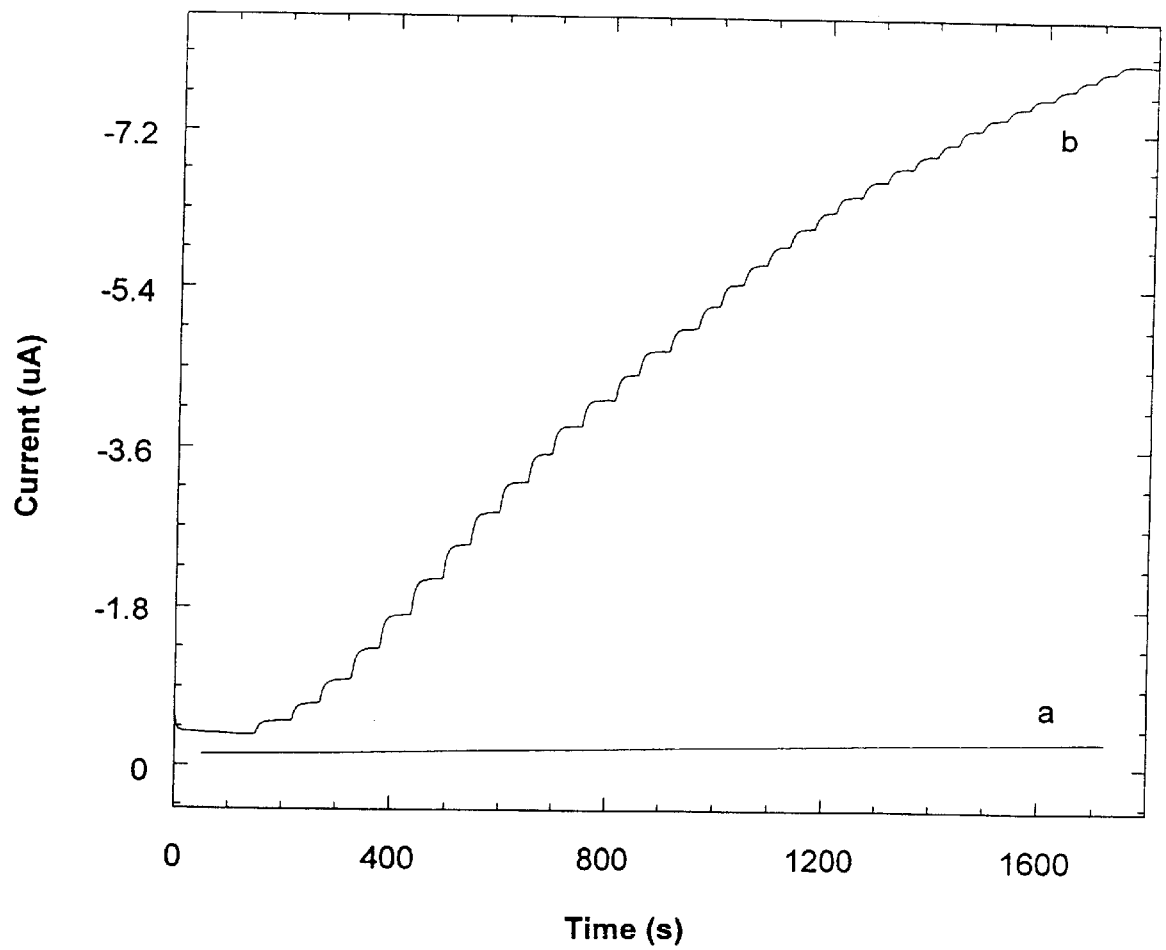
FIG. 8.
Figure 9:
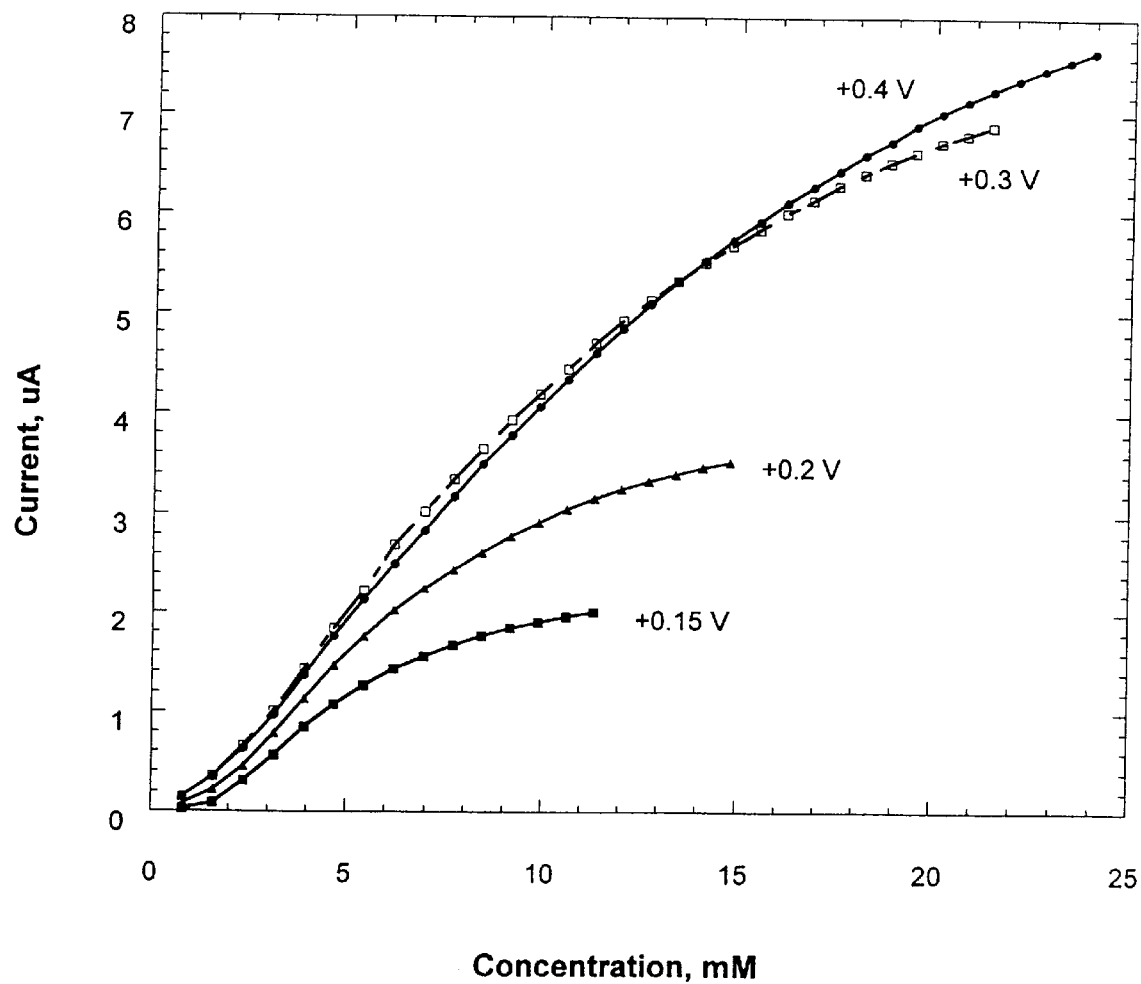
FIG. 9.

A mediated glucose biosensor was prepared and evaluated by incorporating mediator ferrocene and enzyme glucose oxidase into the composite. Cyclic voltammograms in FIG. 7 (solid curves a and b) show the mediated biocatalysis of glucose on the FcGOx modified SSCEs. Curve a shows the redox process of the immobilized Fc in PBS background solution. As shown, the anodic current increased with the addition of glucose (curve b). However, no obvious change occurred on the unmodified electrodes (dashed and dotted curves in FIG. 7). FIG. 8 shows the chronoamperometric responses of glucose on the modified (b) and unmodified (a) SSCEs. No response was observed on the unmodified electrodes, while rapid and sensitive responses occurred on the modified electrodes. Steady-state currents were obtained within 10 seconds, with linearity up to 15 mM and a useful working range from 0.05 mM to 30 mM. Such fast response may be attributed to the absence of any covering membrane and the porous character of the composite surface. FIG. 9 shows the calibration plots for the Fc-GOx modified SSCEs at different applied potentials.

The potential-dependent performances of the modified electrodes are summarized in Table 2.

TABLE 2

Potential-Dependent Performances of the (Ferrocene + $GO_x$) Modified Carbon Strips

| applied potential (mV) | +150 | +200 | +300 | +400 |
|---|---|---|---|---|
| $K^{app}_M$ [a] (mM) | 8.5 | 9.5 | 16.2 | 22.9 |
| $I_s^{max}$ [b] (μA) | 3.5 | 5.8 | 12.1 | 15.0 |
| linear range (mM) | 0–5 | 0–8 | 0–15 | 0–15 |
| sensitivity (μA/mM) | 0.33 | 0.42 | 0.52 | 0.39 |

[a], [b] calculated from $I_s = I_s^{max} - K^{app}_M (I_s/C_s)$
[c] calculated from the linear portion of the calibration curve.

As shown in Table 2, quick background stabilization, rapid response, high sensitivity, and wide linearity were obtained at an applied potential of +0.3 V. Although designed for disposable single-use sensors, these biosensors are very durable and robust. No obvious deterioration in responses were observed for a period of three months with intermittent uses for these sensors kept at room temperature.

It is to be understood that both the foregoing general and detailed description are exemplary and explanatory only and are intended to provide further explanation of the invention, as claimed.

What is claimed is:

1. A method for preparing a surfactant-induced, sol-gel graphite composite electrode, said method comprising the steps of:

mixing an aqueous solution of the surfactant with a silane or a siloxane to obtain a clear and homogeneous sol solution, wherein said mixing is performed in the absence of a co-solvent, a catalyst, or a cellulose binder;

mixing said sol solution with graphite powder to form a uniform and free-flowing paste; and applying said paste onto a substrate to form at least one electrode;

wherein a thermal curing process step is not required.

2. The method of claim 1, wherein the graphite powder is mixed with a buffer solution or an alcohol solution containing a modifier or recognition entity for an analyte, wherein said modifier or recognition entity is chosen according to the analyte to be determined, and dried prior to being mixed with the sol solution.

3. The method of claim 2, wherein the buffer solution or alcohol solution comprises ferrocene and glucose oxidase.

4. The method of claim 2, wherein the alcohol solution is an ethanol solution.

5. The method of claim 1, wherein the substrate is PVC, a ceramic, a metal, or a glass.

6. The method of claim 1, wherein the silane or siloxane is tetramethyl orthosilicate, methyltrimethoxysilane, tetraethoxysilane, or methyltriethoxysilane, and the surfactant is surfactant bis(2-ethylhexyl) sulfosuccinate, octylphenol ethylene oxide condensate, cetyltrimethylammonium bromide, or sodium dodecylsulfate.

7. The method of claim 6, wherein the siloxane is tetramethylorthosilicate and the surfactant is surfactant bis(2-ethylhexyl) sulfosuccinate.

8. The method of claim 1, wherein the paste is applied onto the substrate to form at least one electrode by screen printing.

* * * * *